United States Patent [19]

Wright et al.

[11] Patent Number: 5,268,733
[45] Date of Patent: Dec. 7, 1993

[54] METHOD AND APPARATUS FOR MEASURING CONTACT ANGLES OF LIQUID DROPLETS ON SUBSTRATE SURFACES

[75] Inventors: Richard Wright, Hanover Park; Mark Blitshteyn, Bloomingdale, both of Ill.

[73] Assignee: Tantec, Inc., Schaumburg, Ill.

[21] Appl. No.: 964,217

[22] Filed: Oct. 21, 1992

[51] Int. Cl.[5] .................. G01B 11/26; G01N 13/02
[52] U.S. Cl. .................. 356/150; 356/138; 73/64.52
[58] Field of Search ............ 356/138, 150; 73/64.52

[56] References Cited

U.S. PATENT DOCUMENTS 3,535,043  12/1968  Hong .................... 73/64.52
4,050,822  9/1977  Grat ..................... 73/64.52

FOREIGN PATENT DOCUMENTS 438904  8/1974  U.S.S.R. ................ 73/64.52

Primary Examiner—Richard A. Rosenberger
Assistant Examiner—K. P. Hantis
Attorney, Agent, or Firm—Leydig, Voit & Mayer

[57] ABSTRACT

A method and apparatus for determining the contact angle of a droplet of test liquid on a substrate surface. The apparatus includes a test article support plate, a pipette for depositing a droplet of test liquid onto a substrate surface of the test article, and a lamp for projecting an image of the deposited droplet onto a projection screen with a base line of the image positioned on a horizontal axis line of the screen. The screen further has a protractor scale calibrated to read twice the normal angular value, and a rotatable reference line which upon positioning through a contact point of the droplet with the substrate surface and an apex point of the droplet farthest removed from the substrate surface directly indicates the value of the contact angle of the on the protractor scale.

20 Claims, 1 Drawing Sheet

METHOD AND APPARATUS FOR MEASURING CONTACT ANGLES OF LIQUID DROPLETS ON SUBSTRATE SURFACES

BACKGROUND OF THE INVENTION

1. Field of the Invention

The present invention relates to an improved method and apparatus for determining the contact angle of a liquid droplet on a substrate surface upon which it is deposited.

2. Description of the Prior Art

Contact angle measurements of liquid droplets on substrate surfaces commonly are used to measure wettability of the substrate surface by a liquid and to evaluate adhesion. The contact angle is defined as the angle between the substrate support surface and the tangent to the profile of the droplet at the point of contact of the liquid droplet with the substrate. The value of the contact angle of the liquid droplet will depend upon substrate wettability. If perfect or complete wetting takes place between the liquid and the substrate surface by reason of high surface energy, the droplet will spread out over the substrate surface and the contact angle will approach 0 degrees, whereas if wetting is only partial, the resulting contact angle will lie in the range of 0 to 180 degrees. Devices are known for determining the contact angle of the droplet, both by direct measurement of the angle and by indirect calculation based upon measurements of the height, width, and/or radius of the droplet. Most common procedures involve projecting a silhouette image of the deposited droplet onto a projection screen and determining the contact angle by direct or indirect measurements taken from the silhouette.

Direct measurement of the contact angle is achieved by first establishing a tangent to the profile of the silhouette at the contact point with the substrate and then measuring the angle between the tangent line and the surface of the substrate. This method is subject to significant error. Accurate positioning of a tangent line is difficult since establishing the tangency of a line to an arc is very subjective. As a result, errors as high as 6 degrees can occur.

Indirect measurement of the contact angle can be made by calculation based upon measurements of the droplet silhouette. This method is applicable when the substrate surface is smooth and homogeneous and the droplet is very small, on the order of 10 microliters or smaller, so that the droplet takes the shape of a spherical segment and the distorting effect of gravity is negligible. In such case, the contact angle Θ can be calculate $$\tan \Theta/2 = H/R \quad (1),$$

where H is the drop height and R is the radius of the drop base.

$$\Theta = 2 \times \arctan H/R \quad (2).$$

After the ratio H/R is calculated, the contact angle value can be found in a specially prepared look-up table. This multi-step process is not only time consuming, but is also a subject to error, since the overall chance of error increases with each step of the process.

OBJECTS AND SUMMARY OF THE INVENTION

It is an object of the present invention to provide a method and apparatus for measuring the contact angle of liquid droplets that yields objective and more reliable results.

Another object is to provide a method and apparatus for indirectly determining the contact angle of liquid droplets with a minimal number of steps, and hence, with lesser chance for operator error.

A further object is to provide a contact angle measuring method and apparatus as characterized above which yields reproducible results regardless of who performs the measurement.

Still another object is to provide a contact angle measurement method and apparatus which can be accurately used and carried out without the necessity of complex calculation or reference look-up steps.

Yet another object is to provide a contact angle measurement apparatus that is simple and economical in construction and use.

Other objects and advantages of the invention will become apparent upon reading the following detailed description and upon reference to the drawings, in which:

Figure 1:
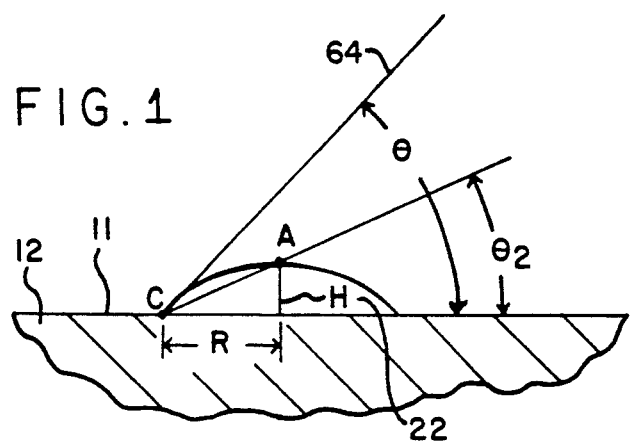
FIG. 1 is a profile view of a droplet of a test liquid on a substrate surface with a graphical representation of the contact angle superimposed thereon.
Figure 2:
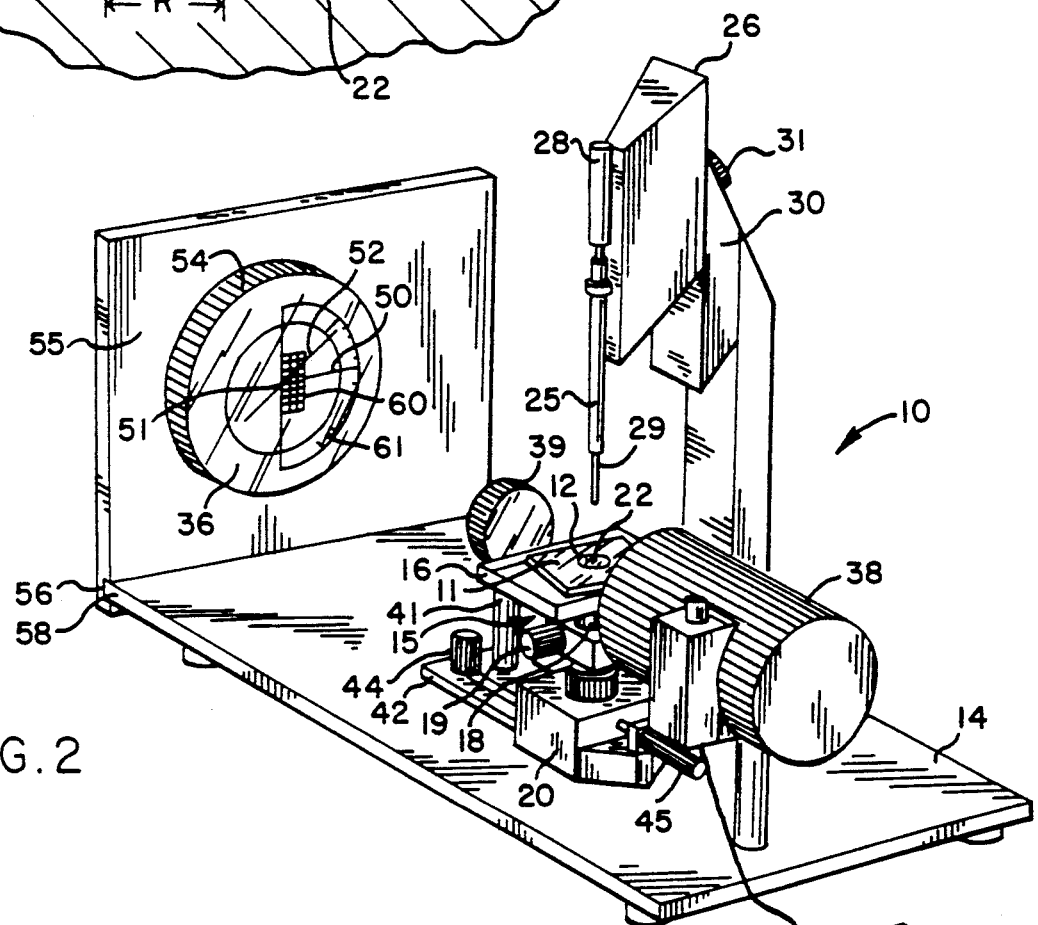
FIG. 2 is a perspective view of the contact angle measuring apparatus of the present invention.

While the invention is susceptible of various modifications and alternative constructions, a certain illustrated embodiment thereof has been shown in the drawings and will be described below in detail. It should be understood, however, that there is no intention to limit the invention to the specific form disclosed, but on the contrary, the intention is to cover all modifications, alternative constructions and equivalents falling within the spirit and scope of the invention.

DETAILED DESCRIPTION OF THE PREFERRED EMBODIMENT

Referring now more particularly to FIG. 1 of the drawings, there is shown an illustrative contact angle measuring apparatus 10 adapted for measuring the contact angle of a liquid droplet of a control substance or test liquid, such as distilled water, applied to a substrate surface 11 of an article or sample 12. The apparatus 10 in this instance is shown for use in determining the surface characteristics of a test article 12 in the form of a flat or co-planar plate. The test article 12 typically will have been surface treated and the contact angle measuring apparatus 10 is utilized for determining the surface characteristics of the test article prior to printing thereon, applying coatings thereto, or use in subsequent manufacturing or assembly procedures. It will be understood that the apparatus of the present invention may be employed to measure the surface characteristics of various articles which are made of plastic, metal or other materials.

The illustrated contact angle measuring apparatus 10 has an elongated platform 14 upon which a test stand 15 is supported. The test article 12 is horizontally positioned on a support plate 16 of the test stand 15 with the substrate surface 11 upwardly directed. For selectively positioning the test article 12 at a desired elevation, the support plate 16 has a depending shaft 18 that appropriately cooperates with the shaft of an adjusting knob 19 in a base 20 of the test stand 15, such as through a threaded coupling, so that rotation of the knob 19 will raise or lower the support plate 16 and the test article 12 supported thereon relative to the base 20 and platform 14 as desired.

For depositing droplets 22 of a test liquid onto the substrate surfaces of test articles 12 positioned on the support plate 16, a pipette 25 is mounted adjacent the test stand 15. The pipette 25 in this case is vertically supported on a slide 26 to one side of the test stand 15 in aligned relation to the test article 12. The pipette 25 is operable in a known manner upon actuation of a plunger 28 for releasing a predetermined liquid droplet 22 from a discharge end or tube 29. The pipette 25 preferably is operable for discharging relatively small sized liquid droplets, such as on the order of 10 microliters or less. For droplets of this size, when applied to a smooth, homogeneous surface, the distorting effect of gravity is negligible, and the droplet will assume the shape of a spherical segment.

For selectively positioning the discharge end 29 of the pipette 25 vertically with respect to the substrate surface 11 of the test article 12, the slide 26 upon which the pipette 25 is mounted is adjustably positionable on a vertical guide 30 mounted on the platform 14. An appropriate locking knob 31 is operable for securing the pipette 25 in the desired vertical position.

In order to project a silhouette image of a deposited liquid droplet 22 onto a projection plane which in this case is in the form of a screen 36, a light beam generating lamp 38 and a magnifying lens 39 are mounted on opposite sides of the test stand 15. The lamp 38 and lens 39 may be of a conventional type, such as sold by Tantec, Inc., assignee of the present application. The lamp 38 is disposed at one end of the platform 14 for projecting a substantially horizontal, calliminated beam of light across the droplet 22 and through the magnifying lens 39, such that a magnified silhouette image 40 of the droplet is projected onto the screen 36 carried on the end of the platform 14 opposite the lamp 38. The magnified image 40 in this instance is projected onto the screen 36 in inverted relation to the horizontal.

To facilitate focusing of the image 40, the lens 39 is carried on a support rod 41 affixed to an adjustably positionable lens mounting plate 42. By loosening a screw 44, the lens plate 42 can be moved longitudinally along the platform 14. Alternatively, minute axial adjustment of the test article support plate 16 can be effected by means of an axial micrometer knob 45 supported on the lamp 38 in fixed relation to the platform 14 for engagement with the base 20 of the test stand base 15, which may be mounted for longitudinal movement on the platform 14.

In accordance with the invention, means are provided (1) for selectively establishing a reference line on the screen in superimposed relation to the droplet image extending between a contact point of the liquid droplet with the substrate surface and an apex point of the liquid droplet farthest removed from the substrate surface and (2) for directly determining the contact angle based upon measurement of the angle between such reference line and a baseline of the droplet as defined by the substrate surface. To this end, the screen 36 has an horizontal axis line 50 with an origin or center point 51, and a hairline reference line 52 is provided for selected rotational movement with respect to the screen 36 about the origin point 51. The horizontal axis line 50 in this case is affixed to the screen 36 and the reference line 52 is on a transparent, circular plastic plate 54, which is appropriately supported on the screen 36 for rotational movement about the origin point 51.

Figure 3:
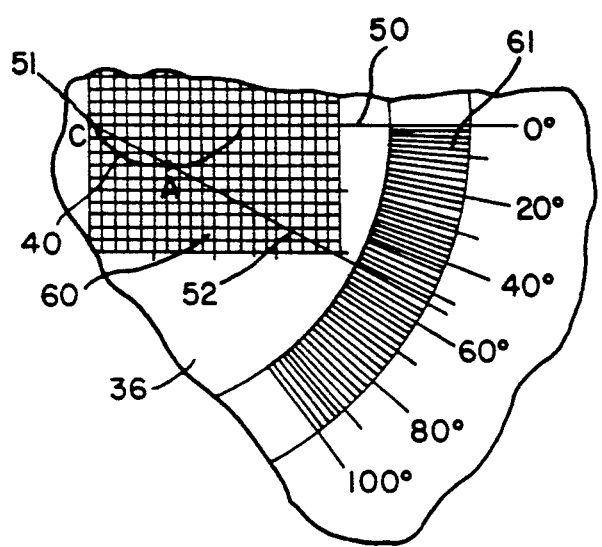
FIG. 3 is a close-up view of a silhouette image of a liquid droplet projected onto a screen of the illustrated apparatus.

By selected vertical adjustment of the test article support plate 16, the image 40 of the droplet 22 may be projected on the screen 36 with the base line of the droplet as defined by the substrate surface 11 coincident with the horizontal axis line 50. To facilitate positioning of a contact point C of the droplet at the origin 51 of the horizontal axis 50, as depicted in FIG. 3, the screen 36 is horizontally positionable with respect to the platform 14. To permit such horizontal positioning of the screen 36, the screen 36 in this case is mounted on a vertical support 55 which may be formed with an appropriate horizontal groove or guide track for receiving a tongue or guide member on a rearward side of the screen to allow for selected horizontal positioning of the screen relative to the support.

In carrying out the invention, with the droplet image 40 properly positioned on the horizontal axis 50 of the screen 36 with the contact point C at the origin point 51, as depicted in FIG. 3, the reference line 52 is selectively rotatable about the origin point 51 to a position where it connects between the origin point C and an apex point A on the droplet image farthest removed from the substrate surface. To facilitate positioning of the reference line 52 through the apex point A, the screen 36 has a grid 60 of closely spaced horizontal and vertical lines.

In keeping with an important feature of the invention, the screen 36 has a fixed protractor scale 61 calibrated to read twice the normal measured angular values for enabling direct and more accurate determination of the contact angle of the liquid droplet by measurement of the angle between the reference line AC and the substrate surface 11. As depicted in FIG. 3, the protractor scale 61 has its center point coincident with the origin point 51 of the horizontal axis 50 and is identical to a conventional protractor scale, except that it is calibrated read twice the normal or actual angular value. In other words, the 20° graduation on the scale depicted in FIG. 3 in actuality is only 10° below the horizontal axis and the 40° graduation depicted in FIG. 3 actually is 20° below the horizontal axis.

A theoretical basis for the operation of the contact angle measuring device of the present invention can be understood by reference to the formula $$\Theta/2 = \arctan H/R \qquad (3)$$

derived from the above shown formula (2), and by reference to FIG. 1 which depicts the liquid droplet profile 22 on the substrate surface 11. As is known in the art, the contact angle $\Theta$ is defined by the angle between the substrate surface 11 and the tangent 64 to the profile of the droplet 22 at the point of contact with the substrate surface 11. According to the formula (3) above, one-half of the contact angle of the droplet 22 is equal to the angle between the substrate surface 11 and the line AC connecting the contact point C and the apex point A of the droplet. Since the angle formed by the line AC and the substrate surface is one-half the contact angle $\Theta$, in the apparatus 10 of the present invention the contact angle can be read directly from the double calculated protractor scale 61.

It will be understood by one skilled in the art that the foregoing theoretical explanation of the contact angle applies to acute contact angles for small droplets on smooth homogeneous surfaces. However, the error is insignificant in a small range of contact angles above 90° such that the apparatus of the present invention can be usefully employed for evaluating and monitoring surface characteristics based upon contacts angles up to about 110-120 degrees.

In operation of the contact angle measuring apparatus 10, a droplet 22 of test liquid may be deposited on the substrate surface 11 of the test article 12 upon actuation of the pipette 25. Upon energization of the lamp 38, a magnified silhouette image 40 of the droplet 22 may be projected onto the screen 36. The image 40 may be brought into precise focus by longitudinal adjustment of the lens 39, and appropriate vertical adjustment of the test article support plate 16 may be made for positioning the base line of the liquid droplet 22 as defined by the substrate surface 11 coincident with the horizontal axis line 50 on the screen. Selected transverse positioning of the screen 36 relative to the support 55 may be made for positioning a contact point C of the liquid droplet 22 coincident with the origin point 51 of the horizontal axis line 50.

Upon the proper positioning of the droplet image 40 onto the screen 36, as depicted in FIG. 3, the reference line 52 may be rotatably positioned, through rotation of the circular plate 54, such that the reference line 52 extends through the contact point C and an apex point A of the droplet farthest removed from the horizontal axis line 50. The grid 60 on the screen 36 facilitates location of the apex point A and proper positioning of the reference line 52.

Upon proper positioning of the reference line 52 through the apex and contact points AC, it will be seen that the contact angle may be reliably determined based upon a measurement of the angle between the reference line 52 and the horizontal axis line 50, which represents one-half the contact angle. Hence, doubling such angle results in the contact angle. In the illustrated embodiment, the contact angle may be directly determined from the double calibrated protector scale 61. As depicted in FIG. 3, while the actual angle between the reference line AC and the horizontal axis line is about 27°, the double calibrated protractor scale permits direct reading of the contact angle as 54°. Hence, it can be seen that the method and apparatus of the present invention eliminate the difficult step of establishing a line of tangency through the contact point, which is subjective and susceptible to significant operator judgment and error.

It will be appreciated by one skilled in the art that while the illustrated contact angle measuring device 10 has been shown for use with a test article 12 in the form of a flat plate, the invention is applicable in determining contact angles of droplets applied to cylindrical or other configured substrate surfaces. Droplets of the test liquid, for example, could be applied to cylindrical shaped test samples in the manner shown in U.S. Pat. No. 5,137,352, assigned to the same assignee as the present application, the disclosure of which is incorporated herein by reference. In that case, the image of the test droplet may be projected onto the screen with a baseline of the droplet as defined by the longitudinal underside of the cylinder positioned on the horizontal axis 50 and a contact point of the droplet at the origin point 51. The contact angle determination can be made in the manner previously described.

From the foregoing, it can be seen that the apparatus and method of the present invention are adapted for determining the contact angles of liquid droplets on substrate surfaces in a manner which yields objective and more reliable results. While the apparatus is adapted for determining the contact angle of liquid droplets by indirect measurement, contrary to the prior art, it requires a minimal number of method steps and does not require complex calculation or reference tables. The apparatus also is both simple and economical in construction and use.

What is claimed is:

1. An apparatus for determining the contact angle of a droplet of test liquid on a substrate surface of an article comprising
    means for supporting the article,
    means for depositing a droplet of test liquid onto said substrate surface,
    a screen,
    means for projecting onto said screen an image of said droplet while supported on said substrate surface,
    means for selectively establishing a reference line on said screen across the droplet image connecting a contact point of the liquid droplet with said substrate surface and an apex point of said liquid droplet farthest removed from said substrate surface, and
    means for determining the contact angle based upon a measurement of the angle between said reference line and said substrate surface.

2. The apparatus of claim 1 in which said screen includes a horizontal axis line having an origin point, means for projecting said image onto said screen with said droplet contact point at said origin point, and means for establishing said reference line through said origin point and the droplet apex point.

3. The apparatus of claim 2 in which said horizontal axis line is fixed to said screen and said reference line is selectively positionable relative to said screen.

4. The apparatus of claim 2 including means for selectively rotating said reference line about said origin point.

5. The apparatus of claim 2 in which said means for determining said contact angle is a protractor scale on said screen having a center coincident with said origin point.

6. The apparatus of claim 5 in which said protractor scale is calibrated to read twice the normal measure angular value.

7. The apparatus of claim 6 in which said reference line is selectively positionable between said origin and apex points for directly indicating on said protractor scale the contact angle of said droplet.

8. The apparatus of claim 2 in which said screen has a grid of vertical and horizontal reference lines against which said droplet image is projected.

9. The apparatus of claim 2 including means for selectively moving at least one of said article supporting means and screen vertically relative to the other for aligning a baseline of said droplet image with said horizontal axis line on said screen.

10. The apparatus of claim 9 including means for selectively adjusting the vertical position of said article supporting means.

11. The apparatus of claim 2 including means for selectively moving at least one of said screen and article supporting means horizontally relative to the other for positioning a contact point of said droplet image at said origin.

12. The apparatus of claim 11 including means for selectively adjusting the horizontal position of said screen.

13. An apparatus for determining the contact angle of a droplet of test liquid on a smooth and homogeneous substrate surface of an article comprising
    means for supporting the article,
    means for depositing a droplet of test liquid of no greater size than about 10 microliters onto said substrate surface,
    a projection plane,
    means for establishing an image of said droplet on said projection plane while supported on said substrate surface,
    means for selectively establishing a reference line on said projection plane across the image connecting a contact point of the liquid droplet with said substrate surface and an apex point of said liquid droplet farthest removed from said substrate surface, and
    means for determining the contact angle based upon a measurement of the angle between said reference line and a base line of said droplet as defined by said substrate surface.

14. The apparatus of claim 13 in which said projection plane has a horizontal axis line having an origin point, means for projecting said image onto said projection plane with said droplet contact point at said origin point and the baseline of the droplet on said horizontal axis line, and means for establishing said reference line through said origin point and said droplet apex point.

15. The apparatus of claim 14 in which said horizontal axis line is fixed to said projection plane and said reference line is rotatable about said origin point.

16. The apparatus of claim 15 in which said means for determining said contact angle is a protractor scale on said projection plane having a center coincident with said origin point and being calibrated to read twice the normal measured value.

17. A method of determining the contact angle of a droplet of test liquid on a horizontal substrate surface of an article comprising the steps of
    applying a droplet of test liquid onto said substrate surface,
    establishing an image of the droplet on a projection plane,
    establishing a reference line on said projection plane across the image connecting a contact point of the liquid droplet with the substrate surface and an apex point of said liquid droplet farthest removed from said substrate surface,
    measuring the angle between said reference line and a base line of the droplet defined by the substrate surface, and
    determining the contact angle of the droplet based upon said measured angle.

18. The method of said claim 17 including determining the contact angle by multiplying the measured angle by two.

19. The method of claim 17 including providing a horizontal axis line with an origin point on said projection plane, projecting an image of said applied droplet onto said projection plane with a base line of the droplet coincident with said horizontal axis and a contact point of the droplet at said origin point, and establishing said reference through said origin point and said droplet apex point.

20. The method of claim 19 including rotating said reference line about said origin point for establishing said reference line through said apex and origin points, and providing a protractor scale on said projection plane calibrated to read twice the normal measured angle value such that positioning of said reference line through said apex and origin points directly indicates the contact angle of the droplet with the substrate surface.

* * * * *